United States Patent [19]

Youssefyeh et al.

[11] Patent Number: 4,874,769

[45] Date of Patent: * Oct. 17, 1989

[54] QUINOLINYL ETHER OR THIOETHER TETRAZOLES AS AGENTS FOR THE TREATMENT OF HYPERSENSITIVE AILMENTS

[75] Inventors: Raymond Youssefyeh, Princeton Junction; Utpal Chakraborty, Flemington, both of N.J.; Ernest Magnien, Norwich, Vt.; Rohit Desai, Millwood; Thomas D-Y Lee, Scarsdale, both of N.Y.

[73] Assignee: Rorer Pharmaceutical Corporation, Fort Washington, Pa.

[ * ] Notice: The portion of the term of this patent subsequent to Dec. 23, 2003 has been disclaimed.

[21] Appl. No.: 124,800

[22] PCT Filed: Mar. 11, 1987

[86] PCT No.: PCT/US87/00560

§ 371 Date: Jan. 5, 1988

§ 102(e) Date: Jan. 5, 1988

[87] PCT Pub. No.: WO87/05510

PCT Pub. Date: Sep. 24, 1987

Related U.S. Application Data

[63] Continuation-in-part of Ser. No. 839,410, Mar. 13, 1986, Pat. No. 4,839,369, and a continuation of Ser. No. 723,781, Apr. 16, 1985, Pat. No. 4,631,287, which is a continuation-in-part of Ser. No. 911,028, Sep. 24, 1986.

[51] Int. Cl.$^4$ .................... A61K 31/47; C07D 265/30; C07D 295/00

[52] U.S. Cl. ...................................... 514/314; 546/152

[58] Field of Search ......................... 514/314; 546/152

Primary Examiner—Stanley J. Friedman

[57] ABSTRACT

This invention relates to certain quinolyl ether and thioether tetrazoles and their use as valuable pharmaceutical agents for the treatment of hypersensitive ailments, particularly as lipoxygenase inhibitors and/or leukotriene antagonists possessing anti-inflammatory and antiallergic properties.

6 Claims, No Drawings

QUINOLINYL ETHER OR THIOETHER TETRAZOLES AS AGENTS FOR THE TREATMENT OF HYPERSENSITIVE AILMENTS

This application ia a continuation-in-part of co-pending U.S. application Ser. No. 839,410 filed Mar. 13, 1986, now U.S. Pat. No. 4,839,369, a continuation of Ser. No. 723,701 filed Apr. 16, 1985, now U.S. Pat. No. 4,631,287, a continuation in part Ser. No. 911,028, filed Sept. 24, 1986.

FIELD OF INVENTION

This invention relates to certain chemical compounds and their use as valuable pharmaceutical agents, particularly as lipoxygenase inhibitors and/or leukotriene antagonists possessing anti-inflammatory and anti-allergic properties.

SUMMARY OF THE INVENTION

This invention relates to the compounds described by the general Formula I and to therapeutic compositions comprising as active ingredient a compound of Formula I:

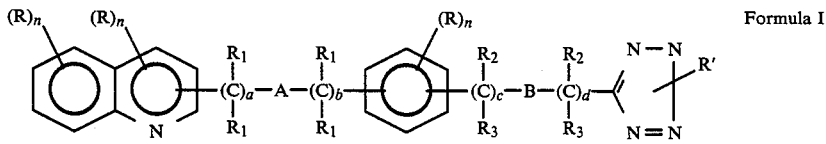

Formula I where:
A is O or S;
B is —$CR_2R_3$—, O or S;
a is 0–2;
b is 0–1;
c is 0–2;
d is 0–5;
n is 0–2;
R is independently hydrogen, alkyl, hydroxy, alkoxy, carbalkoxy, halo, nitro, haloalkyl or cyano;
$R_1$ and $R_2$ are independently hydrogen, alkyl or aralkyl;
vicinal $R_2$ groups together may form a carbon-carbon double-bond;
$R_3$ is —$(CH_2)_x$—X;
where x is 0–3 and
X is hydrogen, alkyl, alkenyl, cycloalkyl, aryl aralkyl, hydroxy, alkoxy, amino, mono- and di-alkylamino, aralkylamino, acylamino, carbamyl, carboxy or carbalkoxy;
vicinal $R_3$ groups together may be —$(CH_2)_y$—where y is 1–4, thus forming a 3–6 membered ring;
geminal $R_2$ and $R_3$ groups may together form a spiro substituent, —$(CH_2)_z$—, where z is 2 to 5;
geminal $R_2$ and $R_3$ groups may together form an alkylidenyl substituent, $$\overset{CHR_4}{\|}$$

where $R_4$ is hydrogen or alkyl;
R' is hydrogen, alkyl or substituted alkyl where the substutuent may be carboxy, carbalkoxy, amino, mono- and di-alkylamino, aralkylamino, acylamino, carbamyl, mono- and di-alkyl carbamyl; and
pharmaceutically acceptable salts thereof.

Preferred compounds of this invention are described by Formulae II and III.

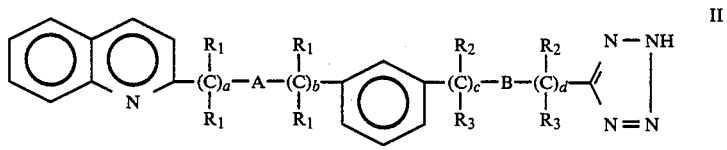

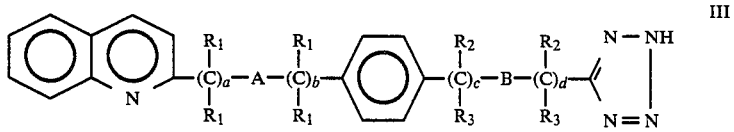

where the substituents are as defined in Formula I.
More preferred compounds are those described by Formula II and III where:
A is O;
B is —$CR_2R_3$—, O, or S;
a is 1–2;
b is 0–1;
c is 0–1;
d is 0–4;
n is 0–1;
R is hydrogen, loweralkyl, hydroxy, loweralkoxy, carboloweralkoxy, halo, nitro, trifuloromethyl or cyano;
$R_1$ and $R_2$ are hydrogen or loweralkyl;
vicinal $R_2$ groups together may form a carbon-carbon double bond;
$R_3$ is —$(CH_2)_x$—X
where x is 0–2 and
X is hydrogen, loweralkyl, cycloloweralkyl, phenyl, hydroxy, lower-alkoxy, amino, mono- and di-loweralkylamino, carbamyl, carboxy or carb-loweralkoxy;
vicinal $R_3$ groups together may be —$(CH_2)_y$— where y is 2–4, thus forming a 4–6 membered ring;
geminal $R_2$ and $R_3$ groups may together form a spiro substituent, —$(CH_2)_z$— where is z 2 to 5;
geminal $R_2$ and $R_3$ groups may together form a loweralkylidenyl substituent, $$\overset{CR_4}{\underset{\|}{}}$$

where $R_4$ is hydrogen or loweralkyl;

R' is hydrogen, loweralkyl or substituted loweralkyl where the substituent may be carboxy, carb-loweralkoxy, amino, mono- and di-alkylamino, acetylamino, carbamyl, mono- and di-loweralkylcarbamyl; and pharmaceutically acceptable salts thereof.

The most preferred compounds are those which form special embodiments by this invention and include those compounds described by Formulae IV and V:

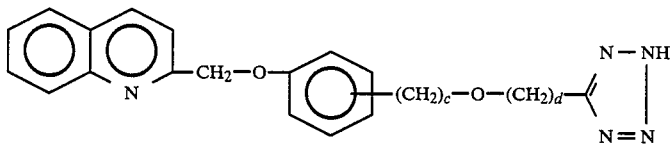

IV

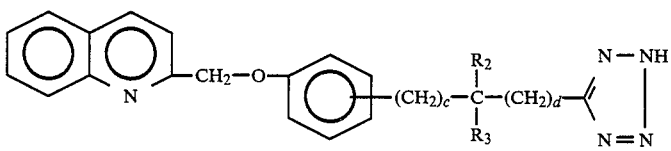

V where:

c, d, $R_2$ and $R_3$ are as described above.

In addition, the present invention relates to the method of using these compounds as lipoxygenase inhibitors and/or leukotriene antagonists possessing antiinflammatory and anti-allergic properties.

As employed above and throughout the disclosure, the following terms, unless otherwise indicated, shall be understood to have the following meanings:

"Alkyl", either alone or with various substituents defined herein, means a saturated aliphatic hydrocarbon, either branched or straight chained. A "loweralkyl" is preferred having about 1 to about 6 carbon atoms. Examples of alkyl include methyl, ethyl, n-propyl, isopropyl, butyl, sec-butyl, t-butyl, amyl, hexyl, etc.

"Alkoxy" refers to a loweralkyl-O-group.

"Alkenyl" refers to a hydrocarbon having at least one point of unsaturation and may be branched or straight chained. Preferred alkenyl groups have six or less carbon atoms present such as vinyl, allyl, ethynyl, isopropenyl, etc.

"Aralkyl" means an alkyl group substituted by an aryl radical. The preferred aralkyl groups are benzyl or phenethyl.

"Cycloalkyl" means a saturated monocyclic hydrocarbon ring having 3 to about 6 carbon atoms such as cyclopropyl, cyclohexyl, etc.

"Acyl" means an organic radical derived from an organic acid by removal of its hydroxyl group. Preferred acyl groups are acetyl, propionyl, benzoyl, etc.

"Halo" means a halogen. Preferred halogens include, chloride, bromide and fluoride. The preferred haloalkyl group is trifluromethyl.

The present compounds can be prepared by art recognized procedures from known compounds or readily preparable intermediates. Exemplary general procedures are as follows:

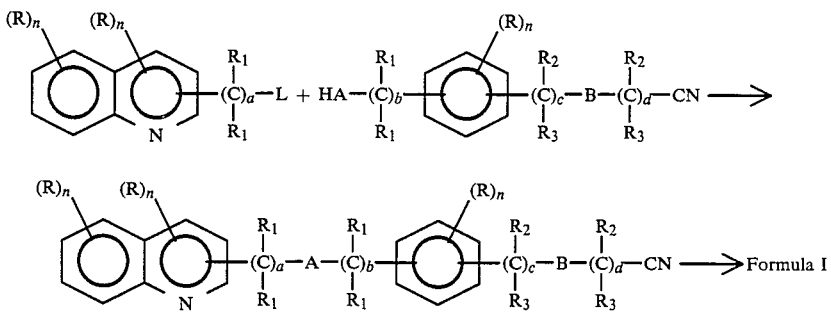

where:

R, $R_1$, $R_2$, $R_3$, a, b, c, d, n, A and B are as defined above, and L is a leaving group, such as halo, tosylate, or mesylate. Where B is O or S, any base normally employed to deprotonate an alcohol or thiol may be used, such as sodium hydride, sodium hydroxide, triethyl amine, sodium bicarbonate or diisopropyl/ethylamine.

Reaction temperatures are in the range of room temperature to reflux and reaction times vary from 2 to 48 hours. The reaction is usually carried out in a solvent that will dissolve both reactants and is inert to both as well. Solvent include, but are not limited to, diethyl ether, tetrahydrofuran, N,N-dimethyl formamide, dimethyl sulfoxide, dioxane and the like.

A further variation for this condensation may involve reactants of the following procedures

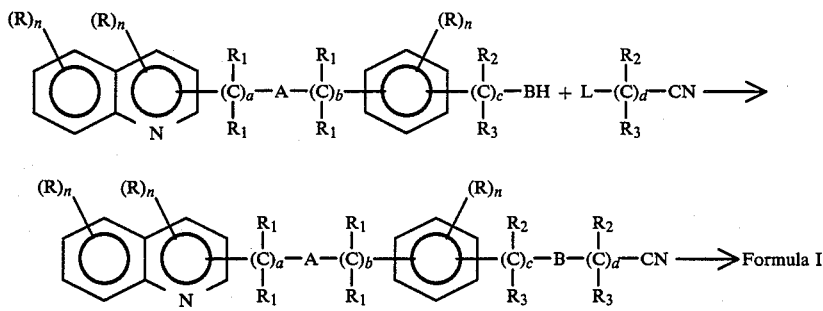

where R, $R_1$, $R_2$, $R_3$, a, b, c, d, n and A are as described above, B is O or S and L is a leaving group as previously described.

Still further, the above reaction sequences may be followed using the tetrazole in place of the nitrile. The tetrazole may be formed at various stages of the synthesis by methods known in the art and it is best to use one which is protected and will not take part in the reaction. One such method would be treating the nitrile with sodium azide in the presence of ammonium chloride in dimethylformamide.

Where B is —$CR_2R_3$— then the starting materials may be prepared from known benzaldehyde or phenyl ketones by reacting these with a Wittig reagent of the formula

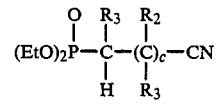

Where vicinal $R_2$ groups together form a carbon-carbon double bond, these compounds also may be prepared by Wittig reaction on the desired benzaldehyde. Thus for example the following schemes may be employed.

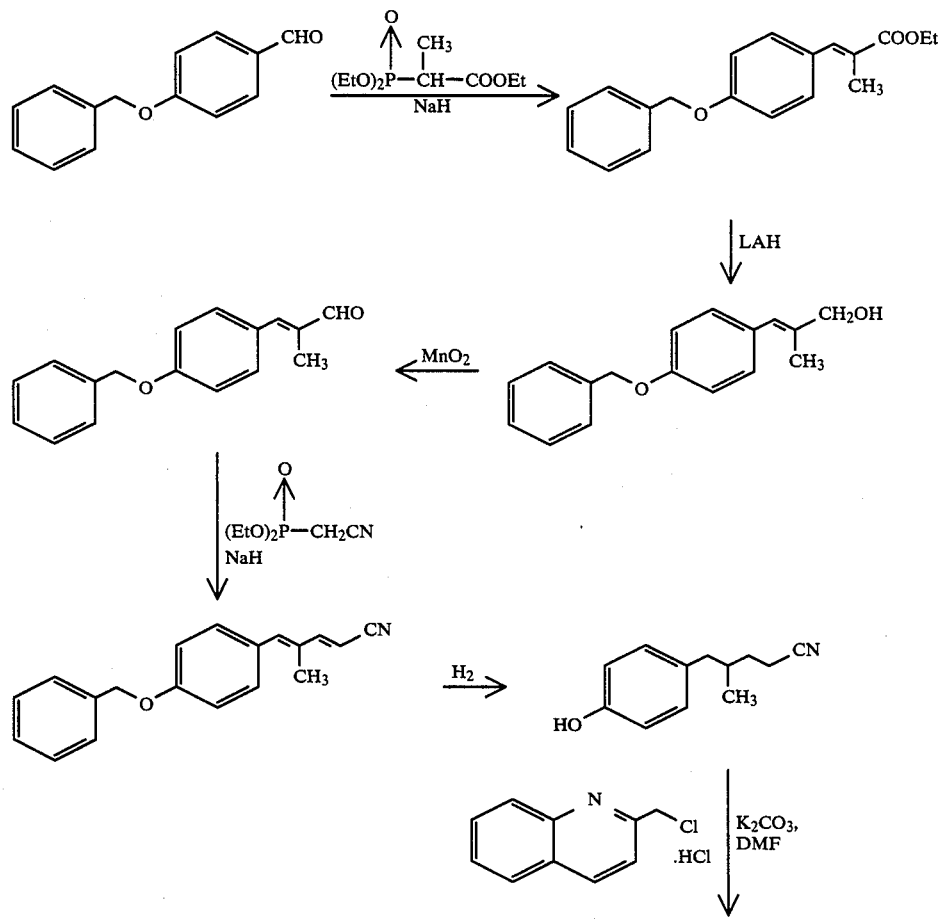

-continued

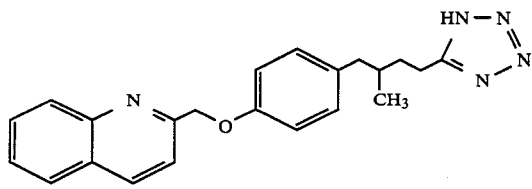 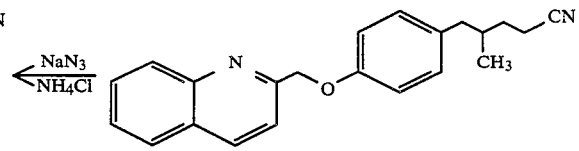

The tetrazole may be formed from the nitrile at various stages of the synthesis.

The products of this invention may be obtained as racemic mixtures of their dextro and levorotatory isomers since at least one asymmetric carbon atom may be present. When two asymmetric carbon atoms are present the product may exist as a mixture of two disastereomers based on syn and anti configurations. These diastereomers may be separated by fractional crystallization. Each diastereomer may then be resolved into dextro and levorotatory optical isomers by conventional methods.

Resolution may best be carried out in the intermediate stage where it is convenient to combine the reacemic compound with an optically active compound by salt formation, ester formation, or amide formation to form two disasteromeric products. If an acid is added to an optically active base, then two disastereomeric salts are produced which posses different properties and different solubilities and can be separated by fractional crystallization. When the salts have been completely separated by repeated crystallization, the base is split off by acid hydrolysis and the pure d and l acids are obtained.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, mailic, tartaric and the like which are pharmaceutically acceptable. Basic salts for pharmaceutical use are the Na, K, Ca and Mg salts.

Various substituents on the present new compounds, e.g., as defined in R, $R_1$, $R_2$ and $R_3$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added to the aromatic ring by nitration and the nitro group converted to other groups, such as amino by reduction, and halo by diazotization of the amino group and replacement of the diazo group. Acyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The compounds of the present invention have potent activity as leukotriene antagonists and as such possess therapeutic value in the treatment of inflammatory conditions and allergic responses such as anaphlaxis and asthma.

Protocol for SRS-A (slow reacting substance of anaphylaxis) Antagonists

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. This protocol describes an in vitro assay used to test compounds which specifically antagonize the actions of leukotrienes.

Peripheral strips of guinea pig lungs are prepared and hung in tissue baths (Metro #ME-5505, 10 ml) according to the published procedure-(Proc. Nat'l. Acad. Sci., U.S.A. Volume 77, pp. 4354-4358, 1980). The strips are thoroughly rinsed in Assay Buffer and then connected with surgical silk thread support rods from the tissue baths. The rods are adjusted in the baths and the strips connected to the pressure transducers (Grass FT 103 or Gould US-3). The tissue baths are aerated with 95% oxygen-5% carbon dioxide and maintained at 37° C. The assay buffer has been made as follows: for each liter of buffer the following are added to approximately 800 ml of water distilled in glass-6.87 g NaCl, 0.4 g $MgSO_4.7H_2O$, and 2.0 g D-glucose. Then a solution of 0.368 g $CaCl_2.2H_2O$ in 100 ml glass-distilled water is slowly added to the buffer. Sufficient water is added to adjust the volume to 1 liter, and the solutin is aerated with 95% oxygen-5% carbon dioxide. Usually 10 liters of buffer are used for an experiment with 4 tissues. After the tissues have been repeatedly washed and allowed to equilibrate in the tissue bath, they are challenged with 1M histamine. After maximum contractions have been obtained, the tissues are washed, and allowed to relax back to baseline tension. this histamine challenge procedure is repeated at least 1 to 2 more times to obtain a repeatable control response. The average response to 1 μM histamine for each tissue is used to normalize all other challenges.

Responses of each tissue to a predetermined concentration of leukotriene are then obtained. Usually test compounds are examined initially at 30 μM on resting tension of the tissues without any added agaonist or antagonist to determine if the compound has any possible intrinsic activity. The tissues are washed and the test compound is added again. Leukotriene is added after the desired pre-incubation time. The intrinsic activity of the compounds, and their effect on leikotriene-induced contractions are then recorded.

The results of this test for of the compounds of the this invention indicates that these compounds are considered to be useful leukotriene antagonists.

Inhibitions of ($^3$H)-LTD$_4$ Binding Membranes from Guinea Pig Lung

A. Preparation of the Crude Receptor Fraction:

This procedure was adapted from Mong et al. 1984).

Male guinea pigs are sacrificed by decapitation and their lungs are quickly removed and placed in a beaker containing ice-cold homgenization buffer. The lungs are separated from connective tissue, minced with scissors, blotted dry and weighed. The tissue is then homogenized in 40 volumes (w/v) of homogenization buffer with a Polytron at a setting of 6 for 30 seconds. The homogenate is centrifuged at 1000×g for 10 minutes (e.g. 3500 RPM, SS-34 Rotor). The supermate is filtered through two layers of cheese cloth and centrifuged at 30,000×g for 30 minutes (e.g. 18,500 RPM SS-34 Rotor), after which the resulting pellet is resuspended in 20 volumes of assay buffer by hand homoginization using a Dounce homogenizer. The final pellet is resuspended in 10 volumes of assay buffer and kept at 4° C. until use.

B. Binding Assay:

Each assay tube (16×100 mm) contains the following:

490 1 Assay Buffer
10 1 Test compound or solvent
100 1 $^3$H-LTD$_4$ (ca. 17,500 DMP)
400 1 Protein preparation Incubations are done at 25° C. for 20 minutes in a shaking water bath. Reactions are started by the addition of the protein preparation. At the end of the incubation time, 4.0 ml of cold wash buffer is added to the tube. After being vortexed, the contents of the tube are immediately poured over a Whatman GF/C Filter (25 mm diameter) which is sitting in a vacuum manifold (e.g., Millipore Model No. 3025 manifold) to which a partial vacuum is applied. The filters are immediately washed with an additional 15 ml of cold buffer. The filters are transferred to 7 ml plastic scintillation vials to which 6.0 ml of appropriate scintillation fluid (e.g., Scintiverse) is added. After being allowed to quilibrate for 4–6 hours, the readioactivity is counted with a liquid scintillation counter appropriately set for tritium.

The required control assay tubes include the following:

(a) Total Binding: No test compound is added; buffer is substituted.

(b) Non-Specific Binding: Non-labeled ligand is added at a concentration of 1 $\mu$M.

(c) Solvent Controls: If test compound is dissolved in a solvent, controls for both Total Binding and Non-Specific Binding containing solvent but no compounds are required.

The results of this test indicate that the compounds for this invention exhibit valuable properties which are useful in the treatment of inflammatory conditions and allergic responses.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and inoils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, wate, ethanol, polyol (for example, glycerol, propylene, glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride, Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those anumerated above. In the case of seterile powders for the preparation of sterile injectable solutions, the preferred methods of preparation are vacum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatement with small dosages by small increments until the optimum effect under the circumstances is reached. The therapeutic dosage will generally be from 0.1 to 100 μM/day or from about 0.1 mg to about 50 mg/kg of body weight per day and higher although it may be administered in several different dosage units. Higher dosages are required for oral administration.

The compounds of the present invention may be prepared by the following representative examples.

EXAMPLE 1

2-[(3-Hydroxyphenoxy)methyl]Quinoline

A mixture of 4.55 g (0.025 mol) resorsinol, 5.35 g (0.025 mol) 2-chloromethylquinoline hydrochloride and 30 ml (2N, NaOH) in 50 ml DMF and 100 ml THF is stirred at 60° C. bath temperature for a period of 3 hours. The reaction mixture is poured into water and extracted with ether. The ether extract is washed with water, dried and concentrated to dryness to obtain the product which is used directly in the next step.

EXAMPLE 2

When 2-chloromethylquinoline of Example 1 above is replaced by the quinoline compounds of Table I below then the corresponding product is obtained.

TABLE I 2-chloromethylquinoline
2-bromomethylquinoline
2-chloroethylquinoline
2-bromoethylquinoline
3-chloromethylquinoline
4-chloromethylquinoline
2-(β-chloroethyl)quinoline
2-(β-chloropropyl)quinoline)
2-(β-chloro-β-phenethyl)quinoline)
2-Chloromethyl-4-methylquinoline
2-Chloromethyl-6-methylquinoline
2-chloromethyl-8-methylquinoline
2-chloromethyl-6-methoxyquinoline)
2-chloromethyl-6-nitroquinoline
2-chloromethyl-6,8-dimethylquinoline

EXAMPLE 3

When resorcinol of Example 1 above is replaced by the compounds of Table II below then the corresponding product is obtained.

TABLE II 1,2-dihydroxybenzene
1,3-dihydroxybenzene
1,4-dihydroxybenzene
2-mercaptophenol
3-mercaptophenol
4-mercaptophenol
1,3-dimercaptobenzene
3-hydroxymethylphenol
3-hydroxyethylphenol
3-mercaptomethylphenol
4-hydroxymethylphenol
4-hydroxyethylphenol
2-methylresorsinol
5-methylresorsinol
5-methyl-1,4-dihydroxybenzene

EXAMPLE 4

When the compounds of Table I, Example 2 are reacted with the compounds of Table II, Example 3 under the conditions of Example 1 then corresponding products are obtained.

EXAMPLE 5

5-(3-Chloropropyl)Tetrazole

A mixture of 3.5 g of 4-chlorobutyronitrile, 2.3 g of sodium azide and 1.9 g of ammonium chloride in 50 ml of dimethylformamide is stirred at 140° C. for 20 hours. The reaction mixture is poured onto ice, basified with 1N sodium hydroxide and extracted twice with ethyl acetate. The aqueous fraction is acidified with acetic acid and extracted with ethylacetate. Evaporation of the ethyl acetate gives 5-(3-chloropropyl)tetrazole which is used directly in the next step.

EXAMPLE 6

When 4-chlorobutyronitrile of Example 5 above is replaced by the nitriles of Table III below then the corresponding tetrazole product is obtained.

TABLE III chloroacetonitrile
bromoacetonitrile
3-chloropropionitrile
4-chlorobutyronitrile
5-chloropentanonitrile
6-chlorohexanonitrile
2-chloropropionitrile
2-methyl-3-chloropropionitrile
2-chlorobutryonitrile

TABLE III-continued 3-chlorobutronitrile
4-methyl-5-chloropentanonitrile
2-methyl-3-chloropropionitrile
3-benzyl-4-chlorobutyronitrile
3-carbethoxymethyl-4-chlorobutryonitrile
3-methoxymethyl-4-chlorobutyronitrile
2,3-dimethyl-4-chlorpentanonitrile
3,3-dimethyl-4-chlorpentanonitrile
spiro(3,3-cyclopropane)-4-chlorbutyronitrile
1-chlormethyl-2-cyanomethylcyclohexane
1-chlormethyl-2-cyanomethylcyclohexane
3-cyclopropylmethyl-4-chlorbutyronitrile
3-dimethylaminomethyl-4-chlorobutyronitrile
3-methylene-4-chlorbutyronitrile
3-propylidene-4-chlorbutyronitrile

EXAMPLE 7

5-[3-(3-(2-Quinolylmethyloxy)Phenoxy)propyl]Tetrazole

A mixture of 3.51 g (0.014 mol) 2-[(3-hydroxyphenoxy)methyl]quinoline, 2.04 g (0.14 mol) 5-(3-chloropropyl)tetrazole and 2 g (0.036 mol) KOH in 5 ml water and 50 ml ethanol is heated over a steam bath for a period of 3 hours. Reaction mixture is concentrated to dryness and slurried into water and extracted with methylene chloride. The methylene chloride extract is washed with water, dried over $MgSO_4$ and concentrated under reduced pressure to obtain solid which is passed through a silica gel column using hexane/ethyl acetate (55:45) as eluent. Evaporation of eluent gives 5-[3-(3-(2-quinolylmethyloxy)phenoxy)propyl]tetrazole (M.P. 147°–149° C.).

EXAMPLE 8

When 2-[(3-hydroxyphenoxy)methyl]quinoline of Example 7 is replaced by the compounds prepared by Examples 2–4 and 5-(3-chloropropyl)tetrazole is replaced by the compounds prepared by Example 6, then the corresponding product is obtained.

EXAMPLE 9

3-[4-(2-Quinolylmethyloxy)Phenoxy]Butyrontrile

A mixture of 17.82 g (0.07 ml) of 2-[(4-hydroxyphenoxy)methyl]quinoline, 7.31 g (0.07 mol) of 4-chlorobutyronitrile and 5.7 g of sodium hydroxide is stirred with 80 ml of dimethyl-sulfoxide at room temperature for 8 hours. The reaction mixture is partitioned between water and ether. The ether extract is evaporated to yield crude product which is purified by passing through a silica gel column using hexane/ethylacetate (3:1) as eluent and the product obtained is used directly in the next step.

EXAMPLE 10

When 2-[(4-hydroxyphenoxy)methyl]quinoline of Example 9 is replaced by the products obtained in Examples 1–4 then the corresponding product is obtained.

EXAMPLE 11

When 4-chlorobutyronitrile of Example 9 is replaced by the nitriles of Table II, Example 6 then the corresponding product is obtained.

EXAMPLE 12

When 2-[(4-hydroxyphenoxy)methyl]quinoline of Example 9 is replaced by the products prepared by Examples 1–4 and 4-chlorbutyronitrile of Example 9 is replaced by the nitriles of Table III, Example 6, then the corresponding products are obtained.

EXAMPLE 13

3-(4-Hydroxyphenoxy)Propionitrile

A mixture of 1.43 g (0.013 mol) 1,4-dihydroxybenzene, 1.15 g (0.013 mol) 3-chloropropionitrile and 15 ml (2N, NaOH) in 15 ml DMF anmd 50 ml THF is stirred overnight at 60° C. bath temperature. The reaction mixture is poured into water and extracted with ether. The ether extract is washed with water, dried and concentrated to dryness under reduced pressure. The residue is passed through a silica gel column using hexane/ethylacetate (3:1) as eluent. Evaporation of eluent gives the desired product which is used directly in the next step.

EXAMPLE 14

When 1,4-dihydroxybenzene of Example 13 is replaced by the compounds of Table II, Example 3 and 3-chloropropionitrle is replaced by the compounds of Table III, Example 6 then the corresponding product is obtained.

EXAMPLE 15

3-[4-(2-Quinolylmethyloxy)phenoxy]propionitrile

A mixture of 2.93 g (0.018 mol) 3-(4-hydroxyphenoxy)propionitrile, 3.2 g (0.18 mol) 2-chlormethylquinoline hydrochloride and 18 ml (2N, NaOH) in 25 ml DMF and 25 ml THF is heated over a steam bath for a period of 24 hours. The reaction mixture is poured into water and extracted with ether. The ether extract is washed with water, dried over $MgSO_4$ and concentrated to dryness under reduced pressure. The residue is passed through a silica gel column using hexane/ethyl acetate (3:1) as eluent to obtain the desired product which is used directly in the next step.

EXAMPLE 16

When 2-chloromethylquinoline of Example 15 is replaced by the quinoline compounds of Table I, Example 2, then the corresponding quinolyl-nitrile products are obtained.

EXAMPLE 17

When 3-(4-hydroxyphenoxy)propionitrile of Example 15 is replaced by the nitriles obtained in Example 14 then the corresponding product is obtained.

EXAMPLE 18

When 2-chloromethylquinoline of Example 15 is replaced by the quinoline compounds of Table I, Example 2 and 3-(4-hydroxyphenoxy)propionitrile is replaced by the nitriles obtained in Example 14, then the corresponding products are obtained.

EXAMPLE 19

5-[2-(4-(2-Quinolylmethyloxy)phenoxy)Ethyl]Tetrazole

A mixture of 9.8 g (0.032 mol) of 3-[4-(2-quinolylmethyloxy)phenoxy]propionitrile, 6.36 g of sodium azide and 5.28 g of ammonium chloride is heated with 30 ml of dry dimethylformamide at 140° C. for 20 hours. The reaction mixture is poured onto ice, basified with 1N sodium hydroxide and extracted 2 times with ethyl acetate. The aqueous fraction is acidified with acetic acid. The product is filtered and washed with water. The crude product is crystallized from acetonitrile to give 5-[2-(4-(2-quinolylmethyloxy)phenoxy)ethyl]tetrazole.

EXAMPLE 20

When 3-[4-(2-quinolylmethyloxy)phenoxy]propionitrile is replaced in Example 19 by the quinolyl-nitrile products obtained in Examples 16–18, then the corresponding product is obtained.

EXAMPLE 21

5-[3-(3-Hydroxyphenoxy)Butyl]Tetrazole

A mixture of 5.9 g of 4-(3-hydroxyphenoxy)valeronitrile, 6.13 g of sodium azide and 5.0 g of ammonium chloride is heated with 30 ml of dry dimethylformamide at 140° C. for 20 hours. The reaction mixture is poured into ice, basified with 1N sodium hyroxide and extracted 2 times with warm ethyl acetate. The aqueous fraction is acidified with acetic acid. The product is filtered and washed with water to give crude product. Crystallization from ethyl acetate gives pure product which is used directly in the next step.

EXAMPLE 22

When 4-(3-hydroxyphenoxy)valeronitrile of Example 21 is replaced by the nitriles of Examples 13 and 14 then the corresponding tetrazole product is obtained.

EXAMPLE 23

5-[3-(3-Hydroxyphenoxy)Butyl]Tetrazole

A mixture of 1.43 g (0.013 mol) 1,3-dihydroxybenzene, 2.1 g (0.013 mol) 5-(3-chlorobutyl)tetrazole and 15 ml (2N, NaOH) in 15 ml DMF and 50 ml THF are stirred overnight at 60° C. bath temperature. The reaction mixture is poured into water and extracted with ether. The ether extract is washed with water, dried and concentrated to dryness under reduced pressure. The residue is passed through a silica gel column using hexane/ethylacetate (3:1) as eluent. Evaporation of eluent gives the tetrazole product which is used directly in the next step.

EXAMPLE 24

When 1,3-dihydroxybenzene of Example 22 is replaced by the compounds of Table II, Example 3, then the corresponding tetrazole is prepared.

EXAMPLE 25

When 5-(3-chlorobutyl)tetrazole of Example 22 is replaced by the tetrazoles prepared by Examples 5 and 6, then the corresponding product is obtained.

EXAMPLE 26

When 1,3-dihydroxybenzene of Example 22 is replaced by the compounds of Table II, Example 3 and 5-(3-chlorobutyl)tetrazole is replaced by the tetrazoles of Example 6, then the corresponding tetrazoles are prepared.

EXAMPLE 27

5-[3-(3-(2-Quinolylmethyloxy)Phenoxy)Butyl]Tetrazole

A mixture of 2.34 g (0.01 mol) 5-[3-(3-hydroxyphenoxy)butyl]tetrazole, 2.13 g (0.01 mol) 2-chloromethylquinoline hydrochloride and 12 ml (2N, NaOH) in 20 ml DMF and 20 ml THF is heated over a steam bath for a period of 24 hours. The reaction mixture is poured into water and extracted with ether. The ether extract is washed with water, dried over MgSO$_4$ and concentrated to dryness under reduced pressure. The residue is passed through a silica gel column using hexane/ethyl acetate (3:1) as eluent. Evaporation of eluent gives 5-[3-(3-(2-quinolylmethyloxy)phenoxy)butyl]tetrazole. (M.P. 147°–149° C.).

EXAMPLE 28

When 5-[3-(3-hydroxyphenoxy)butyl]tetrazole of Example 27 is replaced by the tetrazoles of Example 26 then the coprresponding product is obtained.

EXAMPLE 29

When 2-chloromethylquinoline of Example 27 is replaced by the quinoline compounds of Table I, Example 2, then the corresponding quinolyl-tetrazoles are prepared.

EXAMPLE 30

When 5-[3-(3-hydroxyphenoxy)butyl]tetrazole of Example 27 is replaced by the tetrazoles of Example 26 and 2-chloromethylquinoline is replaced by the quinoline compounds of Table I, Example 2, then the corresponding quinolyltetrazoles are prepared.

EXAMPLE 31

5-[3-(2-Quinolylmethyloxy)Phenyl Tetrazole

A mixture of 8.8 g of 3-(2-quinolylmethyloxy)benzonitrile, 2.3 g of sodium azide and 1.9 g of ammonium chloride in 100 ml of dimethylformamide is stirred at 140° C. for 7 hours. An additional amount of sodium azide (1.2 g) and ammonium (1.0 g) is added and stirring resumed at 140° C. for 17 hours. The mixture is poured over ice and acidified with hydrochloric acid. The crude product solidifies and is filtered off to give 11 g of crude product. The crude product is slurried with hot methanol and filtered off. To a hot solution of this material is added enough water to cause trubidity. On cooling the compound crystallizes and is filtered off to yield 5.0 g of pure material having a M.P. of 200°–205° C. dec.

EXAMPLE 32

Ethyl[5-(3-(2-Quinolylmethyloxy)Phenyl)Tetrazolo]Acetate

To a solution of 0.2 g sodium in 30 ml ethanol is first added 1.1 g of 5-[3-(2-quinolylmethyloxy)phenyl]tetrazole and then after 30 min 0.6 g of ethylbromacetate and stirring is continued at 80° C. for 16 hours.

Solvent is then removed, diluted with water, filtered, washed with ether and dried to give 0.9 g of crude product which is crystallized by ethylacetate/hexane to give 0.6 g product, M.P. 111°–113° C.

When ethylbromoacetate in the above procedure is replaced with N,N-diethyl-α-bromoacetamide; N,N-diethylaminoethyl bromide or N-acetyl-α-bromoacetamide, then the corresponding products are obtained.

EXAMPLE 33

3-[5-(3-(2-Quinolylmethyloxy)Phenyl)Tetrazolo]Acetic Acid

A mixture of 1.3 g of ethyl 3-[5-(3-(2-quinolylmethyloxy)phenyl)tetrazolo]acetate in 5 ml ethanol and 40 ml of 1N NaOH is stirred at 70° C. for 4 hours. It is cooled, diluted with water, acidified with acetic acid, filtered, washed with water, and then ethyl acetate to give 1.0 g product.

EXAMPLE 34

5-[3-(3-(2-Quinolylmethyloxy)Phenoxy)Propyl]Tetrazole

A mixture of 4.4 g of 2-[3-(3-cyanopropoxy)phenoxymethyl]quinoline 2.6 g of sodium azide and 2.1 g of ammonium chloride in 35 ml of dry dimethylformamide is heated at 140° C. for 18 hours. The reaction mixture is poured onto ice. A solution of 20 ml of 1N sodium hydroxide is added and the solution is extracted twice with ethyl acetate. Concentrated hydrochloric acid is added to acidify the aqueous portion. This is extracted twice with ethyl acetate, dried and evaporated to give 4.5 g of a tan solid. Recrystallization from ethyl acetate gives 1.5 g of pure product of M.P. 147°–149° C.

EXAMPLE 35

5-[3-(4-(2-Quinolylmethyloxy)Phenoxy)Propyl]Tetrazole

A mixture of 8.0 g of 4-[4-(2-quinolylmethyloxy)phenoxy]butyronitrile, 4.9 g of sodium azide and 4.0 g of ammonium chloride is heated with 25 ml of dry dimethylformamide at 140° C. for 20 hours. The reaction mixture is poured into ice, basified with 1N sodium hydroxide and extracted 2 times with warm ethyl acetate. The aqueous fraction is acidified with acetic acid. The product is filtered and washed with water to give 6.6 g of crude product. Crystallization from ethyl acetate gives 4.2 g of the light tan product, M.P. 158°–160° C.,

EXAMPLE 36

5-[3-(2-(2-Quinolylmethyloxy)Phenoxy)Propyl]Tetrazole

A mixture of 8.7 g of 4-[2-(2-quinolylmethyloxy)phenoxy]butyronitrile, 5.3 g of sodium azide and 4.4 g of ammonium chloride is heated with 25 ml of dry dimethylformamide at 140° C. for 20 hours. The reaction mixture is poured onto ice, basified with 1N sodium hydroxide and extracted 2 times with ethyl acetate. The aqueous fraction is acidified with acetic acid. The product is filtered and washed with water. The crude product is crystallized from acetonitrile to give 1.7 g of pure product of M.P. 137°–140° C.

EXAMPLE 37

5-[4-(3-(2-Quinolylmethyloxy)Phenoxy)Butyl]Tetrazole

A mixture of 4-[3-(2-quinolymethyloxy)phenoxy]valeronitrile, 5.2 g of sodium azide and 4.3 g of ammonium chloride is heated with 70 ml of dimethylformamide at 140° C. for 20 hours. The reaction mixture is poured onto ice, basified with 1N sodium hydroxide and extracted 2 times with ethyl acetate. The aqueous fraction is acidified with acetic acid and extracted 2 times with ethyl acetate. Evaporation give 5.6 g of product which is crystallized from ethyl acetate to give 4.4 g of product of M.P. 120°–130° C.

EXAMPLE 38

5-[4-(2-Quinolylmethyloxy)Benzyl]Tetrazole

A mixture of 8.6 g of 4-(2-quinolylmethyloxy)benzylnitrile, 6.1 g of sodium azide and 5.0 g of ammonium chloride is heated with 70 ml of dry dimethylformamide at 140° C. for 20 hours. The reaction mixture is poured onto ice, basified with 1N sodium hydroxide and extracted 2 times with ethyl acetate. The aqueous fraction is extracted 2 times with ethyl acetate. Removal of solvent leaves 10.3 g of crude product. This is crystallized from methanol:ethyl acetate to yield 3.3 g of pure product of M.P. 173°–175° C.

EXAMPLE 39

5-[3-Methyl-4-(4-(2-Quinolylmethyloxy)Phenyl)Butyl]-Tetrazole

A. 4-benzyloxy-α-methyl-cinnamic acid ethyl ester. To a solution of sodium hydride (60% oil dispersion, 3.1 g) and triethyl 2-phosphonopropionate (15.5 g) in tetrahydrofuran (50 ml) is added dropwise a tetrahydrofuran solution of 4-benzyloxybenzaldehyde (10.6 g). After stirring at room temperature for 2 hours, the reaction mixture is poured into ice water. The insoluble yellowish solid is collected, purified and used directly in the next step.

B. 4-benzyloxy-α-methyl-cinnamic alcohol. Under argon and with stirring, a tetrahydrofuran solution of 4-benzyloxy-α-methyl-cinnamic acid ethyl ester (11.9 g) is added dropwise to a cooled tetrahydrofuran solution of lithium aluminum hydride (2.5 g). The reaction mixture is allowed to stir for 18 hours and afterward, the excess reagent is destroyed in a conventional manner. The residue which results from the evaporation of the solvent is partioned in a water/ethyl acetate mixture and from the organic layer, there is obtained 7.8 g of a white solid of the desired product. This is used directly in the next step.

C. 4-benzyloxy-α-methyl-cinnamyl aldehyde. Manganese dioxide (15 g total) is added portionwise to a dichloromethane solution (100 ml) of 4-benzyloxymethyl-cinnamic alcohol with stirring over a period of one week. After two filtrations, the filtrate is evaporated to yield a gum. Upon treatment with cold hexane, 4.8 g of product is obtained as white granules and used directly in the next step.

D. 5-(p-benzyloxyphenyl)-4-methyl-2,4-pentaienenitrile. To a solution of sodium hydride (60% oil dispersion, 1.5 g) and diethyl cyanomethylphosphonate (5.4 g) in tetrahydrofuran (50 ml) is added dropwise a tetrahydrofuran solution of 4-benzyloxy-methyl-cinnamyl aldehyde (4.8 g). After stirring at room temperature for 2 hours, the reaction mixture is poured into ice water. The insoluble material is collected to obtain 4.6 g of off-white solid, after purification this is used directly in the next step.

E. 5-p-hydroxyphenyl-4-methylvaleronitrile. 5-(p-Benzyloxyphenyl)-4-methyl-2,4-pentadienetrile (4.3 g) dissolved in ethanol is hydrogenated (0.8 g of 5% palladium over charcoal as catalyst) around 30 psi overnight. After filtering off the catalyst, the solvent is evaporated to give an oil (2.9 g). This is used directly in the next step.

F. 4-methyl-5-[4-(2-quinolylmethyloxy)phenyl]-valeronitrile. A reaction mixture of 5-p-hydroxyphenyl-4-methyl-valeronitrile (2.9 g, 2-chloromethylquinoline hydrochloride (4.2 g) and anhydrous potassium carbonate (30 g) in dimethylformamide (60 ml) is stirred and heated (110° C.) for 5 hours. Afterward, the solvent is removed under vacuum and the residue is partioned in a mixture of chloroform/water. The organic layer is evaporated and the resultant oil is purified on a silica gel dry column (chloroform as eluant) to give 2.3 g of an off-white solid. This is used directly in the next step.

G. 5-[3-methyl-4-(4-(2-quinolylmethyloxy)phenyl)-butyl]tetrazole. A mixture of 4-methyl-5-[4-(2-quinolylmethyloxy)phenyl]valeronitrile (1.5 g), sodium azide (3 g), ammonium chloride (2.8 g) in dimethylformamide (20 ml) is stirred and heated at 135° C. for 18 hours. After cooling, the reaction mixture is poured into ice water and the insoluble material is taken up by chloroform. The residue from the evaporation of chloroform is purified by silica gel dry column (5% methanol in chloroform as eluant) twice followed by trituration with ether/hexane to yield 5-[3-methyl-4-(4-(2-quinolylmethyloxy)phenyl)butyl]tetrazole. (0.7 g M.P. 75°–77° C.

EXAMPLE 40

When 2-chloromethylquinoline of Example 39, Part F is replaced by the quinoline compounds of Table I Example 2, then the corresponding product is obtained. When the products are treated according to the the procedures of Steps F and G, then the corresponding tetrazole products are obtained.

EXAMPLE 41

When 5-p-hydroxyphenyl-4-methylvaleronitrile of Example 39, Part E is used in Example 21 in place of 4-(3-hydroxyphenoxy)valeronitrile, then the product obtained is 5-[3-methyl-4-(p-hydroxyphenyl)butyl]tetrazole. When this product is treated according to Step F of Example 39, the same product is obtained.

EXAMPLE 42

When triethyl 2-phosphonopropionate of Example 39, Step A is replaced by the Witting reagents of Table IV below then the correspondig products are obtained.

TABLE IV triethyl 2-phosphonoacetate
triethyl 2-phosphonopropionate
triethyl 3-phosphonopropionate
triethyl 4-phosphonobutyrate
triethyl 3-phosphonobutyrate
triethyl 2-phosphonobutyrate
triethyl 5-phosphonopentanoate
triethyl 4-phosphonopentanoate
triethyl 3-phosphonopentanoate
triethyl 4-phosphono-3-methylbutyrate
triethyl 4-phosphono-2,3-dimethylbutyrate
triethyl 5-phosphono-4-methylpentanoate
triethyl 5-phosphono-3,4-dimethylpentanoate
triethyl 4-phosphono-3,3-dimethylbutyrate
triethyl 4-phosphono-3-phenylbutyrate
triethyl 4-phosphono-3-benzylbutyrate
triethyl 3-phosphono-2,2-dimethylpropionate
triethyl 4-phosphono-2-propylbutyrate
triethyl 4-phosphono-3-propylbutyrate
triethyl 3-phosphonomethylhexanoate
triethyl 4-phosphonoheptanoate

EXAMPLE 43

When diethylcyanomethylphosphonate of Example 39, Step D is replaced by the Wittig reagents of Table V below then the corresponding products are obtained.

TABLE V diethyl 2-phosphonoacetonitrile
diethyl 3-phosphonopropionitrile
diethyl 2-phosphonopropionitrile
diethyl 4-phosphonobutyronitrile
diethyl 3-phosphonobutyronitrile

TABLE V-continued diethyl 2-phosphonobutyronitrile
diethyl 5-phosphonopentanonitrile
diethyl 4-phosphonopentanonitrile
diethyl 3-phosphonopentanonitrile
diethyl 2-phosphonopentanonitrile
diethyl 4-phosphono-5-phenylpentanonitrile
diethyl 4-phosphono-3-phenylbutyronitrile
diethyl 4-phosphono-5-cyclopropylpentanonitrile
diethyl 4-phosphonohexanonitrile
diethyl 4-phosphonoheptanonitrile
diethyl 4-phosphono-5-carbethoxypentanonitrile
diethyl 4-phosphono-3-methylenebutyronitrile
diethyl 4-phosphono-3-ethylidenebutyronitrile
diethyl 1-phosphonomethyl-1-cyanoethylcyclopropane
diethyl 1-phosphonomethyl-1-cyanomethylcyclobutane
diethyl 1-phosphonomethyl-2-cyanomethylcyclobutane
diethyl 1-phosphonmethyl-2-cyanomethylcyclopentane

EXAMPLE 44

When triethyl 2-phosphonopropionate of Example 39, Step A is replaced by the Wittig reagents of Table V, Example 43, then the corresponding products are obtained. When these products are treated according to the procedure of Example 40, then the corresponding product is obtained.

EXAMPLE 45

Following the above procedures the following compounds may be prepared.

5-[4-(2-quinolylmethyloxy)benzyl]tetrazole M.P. 173°–175° C.

5-[4-(3-(2-quinolylmethyloxy)phenoxy)butyl]tetrazole M.P. 129°–130° C.

5-[3-(2-(2-quinolylmethyloxy)phenoxy)propyl]tetrazole M.P. 137°–140° C.

5-[3-(4-(2-quinolylmethyloxy)phenoxy)propyl]tetrazole M.P. 158°–160° C.

5-[3-(3-(2-quinolylmethyloxy)phenoxy)propyl]tetrazole M.P. 150°–151° C.

5-[3-(2-quinolylmethyloxy)phenyl]tetrazole M.P. 214°–216° C.

5-[3-(4-(2-quinolylmethyloxymethyl)phenoxy)-propyl]tetrazole M.P. 114°116° C.

5-[3-methyl-4-(4-(2-quinolylmethyloxy)phenyl)-butyl]tetrazole M.P. 75°–77° C.

5-[4-(4-(2-quinolylmethyloxy)phenyl)butyl]tetrazole M.P. 124°–127° C.

5-[2-(4-(2-quinolylmethyloxy)phenyl)ethyl]tetrazole M.P. 162° C. dec

5-[3-(5-methyl-3-(2-quinolylmethyloxy)phenoxy)-propyl]tetrazole M.P. 108°–112° C.

5-[3-(2-ethyl-5-(2-quinolylmethyloxy)phenoxy)-propyl]tetrazole M.P. 139°–140° C.

5-[3-(4-(2-quinolylmethylthio)phenoxy)propyl]tetrazole M.P. 141°–143° C.

5-[3-(2-methyl-4-(2-quinolylmethyloxy)phenoxy)-propyl]tetrazole M.P. 72°–73° C.

5-[3-(3-(2-quinolylmethyloxy)phenoxy)propyl]tetrazole HCl M.P. 215°–218° C.

5-[3-(4-(2-quinolylmethyloxy)thiophenoxy)propyl]-tetrazole M.P. 122°–124° C.

5-[3-(4-(2-(6-methoxy)quinolylmethyloxy)phenoxy)-propyl]tetrazole M.P. 165°–167° C.

5-[3-(4-(2-(5-bromo-6-methoxy)quinolylmethyloxy)-phenoxy)propyl]tetrazole M.P. 181°–183° C.

5-[(3-(2-quinolylmethyloxy)phenoxy)methyl]tetrazole M.P. 188°–190° C.

ethyl-3-[5-(3-(2-quinolylmethyloxy)phenyl)tetrazolo]acetate M.P. 111°–113° C.

5-[3-(2-quinolylmethyloxy)phenyl]tetrazole M.P. 214°–216° C.

5-[4-(2-quinolylmethyloxy)styryl]tetrazole M.P. 245° C. dec

5-[3-(2-quinolylmethyloxy)styryl]tetrazole M.P. 201° C. dec

EXAMPLE 46

Following the above procedures the following compounds may be prepared.

5-[4-(3-(2-quinolymethyloxy)phenyl)butyl]tetrazole
5-[1-methyl-4-(3-(2-quinolylmethyl)phenyl)butyl]tetrazole
5-[2-methyl-4-(3-(2-quinolylmethyloxy)phenyl)butyl]-tetrazole
5-[3-methyl-4-(3-(2-quinolylmethyloxy)phenyl)butyl]-tetrazole
5-[4-methyl-4-(3-(2-quinolylmethyloxy)phenyl)butyl]-tetrazole
5-[1-propyl-4-(3-(2-quinolylmethyloxy)phenyl)butyl]-tetrazole
5-[2-propyl-4-(3-(2-quinolylmethyloxy)phenyl)butyl]-tetrazole
5-[3-propyl-4-(3-(2-quinolylmethyloxy)phenyl)butyl]-tetrazole
5-[4-propyl-4-(3-(2-quinolylmethyloxy)phenyl)butyl]-tetrazole
5-[1-phenyl-4-(3-(2-quinolylmethyloxy)phenyl)butyl]-tetrazole
5-[2-phenyl-4-(3-(2-quinolylmethyloxy)phenyl)butyl]-tetrazole
5-[3-phenyl-4-(3-(2-quinolylmethyloxy)phenyl)butyl]-tetrazole
5-[4-phenyl-4-(3-(2-quinolylmethyloxy)phenyl)butyl]-tetrazole
5-[1-benzyl-4-(3-(2-quinolylmethyloxy)phenyl)butyl]-tetrazole
5[2-benzyl-4-(3-(2-quinolylmethyloxy)phenyl)butyl]tetrazole
5-[3-benzyl-4-(3-(2-quinolylmethyloxy)phenyl)butyl]-tetrazole
5-[4-benzyl-4-(3-(2-quinolylmethyloxy)phenyl)butyl]-tetrazole
5-[2,3-dimethyl-4-(3-(2-quinolylmethyloxy)phenyl)-butyl]tetrazole
5-[3,3-dimethyl-4-(3-(2-quinolylmethyloxy)phenyl)-butyl]tetrazole
5-[1,3-dimethyl-4-(3-(2-quinolylmethyloxy)phenyl)-butyl]tetrazole
5-[4-carboxymethyl-4-(3-(2-quinolylmethyloxy)-phenyl)butyl]tetrazole
5-[4-hydroxycarboxymethyl-4-(3-(2-quinolylmethyloxy)phenyl)butyl]tetrazole
5-[3-carboxymethyl-4-(3-(2-quinolylmethyloxy)-phenyl)butyl]tetrazole
5-[3-carboxy-4-(3-(2-quinolylmethyloxy)phenyl)butyl]-tetrazole
5-[4-(4-(2-quinolylmethyloxy)phenyl(butyl]tetrazole
5-[1-methyl-4-(4-(2-quinolylmethyloxy)phenyl)butyl]-tetrazole
5-[2-methyl-4-(4-(2-quinolylmethyloxy)phenyl)butyl]-tetrazole
5-[3-methyl-4-(4-(2-quinolylmethyloxy)phenyl)butyl]-tetrazole
5-[4-methyl-4-(4-(2-quinolylmethyloxy)phenyl)butyl]-tetrazole
5-[1-propyl-4-(4-(2-quinolylmethyloxy)phenyl)butyl]-tetrazole
5-[2-propyl-4-(4-(2-quinolylmethyloxy)phenyl)butyl tetrazole
5-[3-propyl-4-(4-(2-quinolylmethyloxy)phenyl)butyl]-tetrazole
5-[4-propyl-4-(4-(2-quinolylmethyloxy)phenyl)butyl]-tetrazole
5-[1-phenyl-4-(4-(2-quinolylmethyloxy)phenyl)butyl]-tetrazole
5-[2-phenyl-4-(4-(2-quinolylmethyloxy)phenyl)butyl]-tetrazole
5-[3-phenyl-4-(4-(2-quinolylmethyloxy)phenyl)butyl]-tetrazole
5-[4-phenyl-4-(4-(2-quinolylmethyloxy)phenyl)butyl]-tetrazole
5-[1-benzyl-4-(4-(2-quinolylmethyloxy)phenyl)butyl]-tetrazole
5-[2-benzyl-4-(4-(2-quinolylmethyloxy)phenyl)butyl]-tetrazole
5-[3-benzyl-4-(4-(2-quinolylmethyloxy)phenyl)butyl]-tetrazole
5-[4-benzyl-4-(4-(2-quinolylmethyloxy)phenyl)butyl]-tetrazole
5-[2,3-dimethyl-4-(4-(2-quinolylmethyloxy)phenyl)butyl tetrazole
5-[3,3-dimethyl-4-(4-(2-quinolylmethyloxy)phenyl)-butyl]tetrazole
5-[1,3-dimethyl-4-(4-(2-quinolylmethyloxy)phenuyl)-butyl]tetrazole
5-[4-carboxymethyl-4-(4-(2-quinolylmethyloxy)-phenyl)butyl]tetrazole
5-[4-hydroxycarboxymethyl-4-(4-(2-quinolylmethyloxy)phenyl)butyl]tetrazole
5-[3-carboxymethyl-4-(4-(2-quinolylmethyloxy)-phenyl)butyl]tetrazole
5-[3-carboxy-4-(4-(2-quinolylmethyloxy)phenyl)butyl]-tetrazole

We claim:

1. A compound selected from the group consisting of 5-[3-(2-ethyl-5-(2-quinolylmethyloxy)phenoxy)propyl]-tetrazole, 5-[3-(2-methyl-4-(2-quinolylmethyloxy)-phenoxy)propyl]tetrazole, 5-[3-(5-methyl-3-(2-quinolylmethyloxy)phenoxy)propyl]tetrazole, 5-[3-(4-(2-(5-bromo-6-methoxy)quinolylmethyloxy)phenoxy)-propyl]tetrazole, 5-[3-(4-(2-(6-methoxy)quinolylmethyloxy)phenoxy)propyl]tetrazole, 5-[3-(4-(2-quinolylmethylthio)phenoxy)propyl]tetrazole, 5-[3-(4-(2-quinolylmethyloxy)thiophenoxy)propyl]tetrazole, 5-[2-(4-(2-quinolylmethyloxy)phenyl)ethyl]tetrazole, 5-[4-(4-(2-quinolylmethyloxy)phenyl)butyl]tetrazole and 5-[(3-(2-quinolylmethyloxy)phenoxy)methyl]tetrazole.

2. A compound which is 5-[3-methyl-4-(4-(2-quinolylmethyloxy)phenyl)butyl]tetrazole.

3. A pharmaceutical composition for use in treating inflammatory or allergic conditions comprising in admixture with a pharmaceutically acceptable carrier an effective anti-inflammatory or anti-allergic amount of a compound according to claim 1.

4. A pharmaceutical composition for use in treating inflammatory or allergic conditions comprising in admixture with a pharmaceutically acceptable carrier an effective anti-inflammatory or anti-allergic amount of a compound according to claim 2.

5. A method for the treatment of hypersensitive ailments in humans and mammals comprising administering thereto an effective amount of a compound according to claim 1.

6. A method for the treatment of hypersensitive ailments in humans and mammals comprising administering thereto an effective amount of a compound according to claim 2.

* * * * *